(12) United States Patent
Jalde et al.

(10) Patent No.: US 6,443,154 B1
(45) Date of Patent: Sep. 3, 2002

(54) APPARATUS FOR THE SUPPLY OF A BREATHING GAS

(75) Inventors: Fredrik Jalde, Stockholm; Göran Skog, Bromma; Per-Göran Eriksson; Bo Lundin, both of Täby, all of (SE)

(73) Assignee: Siemens-Elema AB, Solna (SE)

( * ) Notice: Subject to any disclaimer, the term of this patent is extended or adjusted under 35 U.S.C. 154(b) by 30 days.

(21) Appl. No.: 09/585,534

(22) Filed: Jun. 2, 2000

(30) Foreign Application Priority Data

Jun. 10, 1999 (SE) .............................................. 9902180

(51) Int. Cl.⁷ .............................. A62B 7/10; A62B 23/02
(52) U.S. Cl. ............................ 128/205.29; 128/204.24; 128/204.25; 128/201.28; 128/204.26; 128/205.12; 128/204.18
(58) Field of Search ....................... 128/205.19, 204.24, 128/204.25, 204.23, 201.28, 204.26, 205.24, 205.12, 204.18

(56) References Cited

U.S. PATENT DOCUMENTS

| | | | |
|---|---|---|---|
| 3,812,878 A | | 5/1974 | Bird et al. |
| 3,844,280 A | | 10/1974 | Smythe |
| 4,182,599 A | * | 1/1980 | Eyrick et al. ................ 417/328 |
| 4,796,618 A | * | 1/1989 | Garraffa ................. 128/204.26 |
| 4,877,023 A | * | 10/1989 | Zalkin .................... 128/204.21 |
| 4,883,051 A | * | 11/1989 | Westenskow et al. .. 128/204.21 |
| 5,040,529 A | * | 8/1991 | Zalkin .................... 128/204.18 |
| 5,303,698 A | * | 4/1994 | Tobia et al. ........... 128/204.21 |
| 5,507,282 A | * | 4/1996 | Younes ................... 128/204.21 |
| 5,632,270 A | * | 5/1997 | O'Mahony et al. ..... 128/204.24 |
| 5,664,562 A | * | 9/1997 | Bourdon ................. 128/204.23 |
| 5,664,563 A | * | 9/1997 | Schroeder et al. ...... 128/204.25 |
| 5,678,541 A | * | 10/1997 | Garraffa ................. 128/205.24 |
| 6,158,432 A | * | 12/2000 | Biondi et al. .......... 128/204.21 |
| 6,286,505 B1 | * | 9/2001 | Psaros .................... 128/203.12 |

FOREIGN PATENT DOCUMENTS

| | | |
|---|---|---|
| EP | 0 697 224 | 2/1996 |
| EP | 0 700 690 | 3/1996 |
| EP | 0 813 883 | 4/1997 |

* cited by examiner

*Primary Examiner*—Aaron J. Lewis
*Assistant Examiner*—Darwin P. Erezo
(74) *Attorney, Agent, or Firm*—Schiff Hardin & Waite

(57) ABSTRACT

An apparatus for supplying a breathing gas to a patient has a gas supply for generating a flow of breathable gas during an inspiration and an expiration phase of a patient breathing cycle. An inspiration line is provided having an inlet through which a flow of breathing gas from the supply can pass as well as an expiration line through which an expiration gas from the patient can flow. A flow controller is provided for selecting, during an inspiration phase, a first flow path for gas from the supply into the inlet and for selecting, during the expiration phase, a second flow path for gas from the supply in a direction across a venturi outlet of the expiration line, to enhance removal of expiration gas therefrom by venturi suction.

7 Claims, 3 Drawing Sheets

APPARATUS FOR THE SUPPLY OF A BREATHING GAS

BACKGROUND OF THE INVENTION

1. Field of the Invention

The present invention relates to an apparatus for the supply of a breathing gas to a patient.

2. Description of the Prior Art

An apparatus, such as a ventilator or respirator, for supplying a breathing gas to a patient, in which a supply means is operated to continuously generate a flow of gas, is disclosed in European Application 0 813 883. The apparatus disclosed therein has a fan or compressor which may be continuously operated to provide a flow of a breathable gas to a flow divider. The flow divider operates to divert the gas flow either toward a patient during an inspiration phase of the patient's breathing cycle or to a recirculating system during an expiration phase, to be re-directed toward the patient in the subsequent inspiration phase. Since the supply means is operated continuously, changes in supply to the patient can be made rapidly by varying only the relatively responsive flow divider. The gas supplied by the supply means, however, is not usefully employed during the expiration phase and the energy used in powering the supply means may be considered as being wasted.

SUMMARY OF THE INVENTION

It is an object of the present invention to provide an apparatus in which gas supplied by a supply arrangement can be usefully employed during an expiration phase of a patient.

By providing the expiration tube with a venturi outlet and arranging for gas from the supply to pass across this outlet, preferably at an angle of 90° or less to the direction of expiration gas flow from the outlet, during an expiration phase then expiration effort expended by the patient can be reduced.

The supply, such as a compressor or fan assembly, can be operated to continuously generate a flow of breathable gas throughout the patient's breathing cycle. This has the advantage that no additional gas source need be included within the supply for supplying gas during the expiration phase.

A vane deflector, rotatable in the flow path of the gas from the supply, for selectively coupling the flow to the inspiration or expiration lines may be used. This provides a relatively simple and inexpensive flow controller.

Additionally, the supply can be operated to provide a flow greater than that required during an inspiration phase. This means that the vane need not deflect all gas flow into the inspiration line. This avoids problems, such as incorrect switching between the inspiration and the expiration phases, associated with the vane sticking against a sealing surface and also allows a less expensive vane deflector to be used since manufacturing tolerances are reduced compared to a deflector in which a complete seal must be effected.

The venturi outlet may be variable in size to allow control of the venturi effect and hence the expiration effort of a patient. This may be simply achieved by arranging for the vane of the vane deflector to be cooperable with the end of the expiration line to form a venturi outlet that varies as the deflector moves.

DESCRIPTION OF THE PREFERRED EMBODIMENTS

Figure 1:
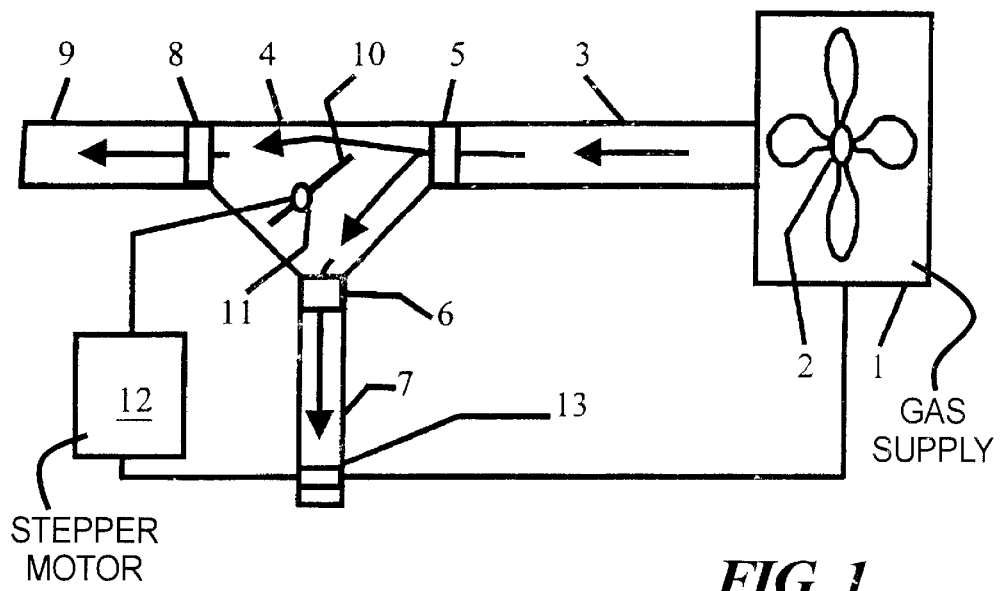
FIG. 1 is a schematic representation of a portion of a ventilator of the present invention.

FIG. 1 illustrates a patient ventilator which has a breathing gas supply 1 including a fan assembly 2 for providing an air flow continuously throughout the breathing cycle of a patient along a flow path defined, in part, by a delivery conduit 3 and a flow controller 4 connected to one end of the conduit 3 at an inlet 5. The controller 4 is provided with a common inlet/outlet 6 which connects to one end of a breathing tube 7. An opposite end of the tube 7 is connectable to a patient's airways (not shown) when the ventilator is in use and provides a flow path for inspiration gas to the airways and for expiration gas from the airways in a manner conventional in the art of patient ventilation. The flow controller 4 is also provided with an outlet 8 connected to an exhaust line 9 which is here vented to atmosphere. Thus, the flow path of gas from the fan 2 divides into two parts within the flow controller 4; one path leads gas from the inlet 5 to the outlet 8; and one path leads gas from the inlet 5 to the common inlet/outlet 6. These paths are illustrated in FIG. 1 by the arrows. A deflector, in the form of a vane 10, mounted on an axle 11 of a stepper motor 12 is also included as part of the flow controller 4. The vane 10 is located in the flow path of the gas from the supply 1 that enters the controller via the inlet 5 and may be rotated to vary the division of the gas flow to the openings 6, 8 of the flow controller 4. As shown in the embodiment of FIG. 1 a flow sensor 13 may be provided in the breathing tube 7 to sense gas flow therethrough and to provide the magnitude (and optionally direction) of the sensed flow as a control signal to the stepper motor 12 which then rotates the axle 11 to vary the inclination of the vane 10 and achieve a desired flow in the breathing tube 7. Optionally, as also shown in FIG. 1, the output from the sensor 13 may also be used to provide a control signal to the supply 1. This control signal may be used to vary the rotational speed of the fan 2 to assist in achieving the desired gas flow.

Figure 2A:
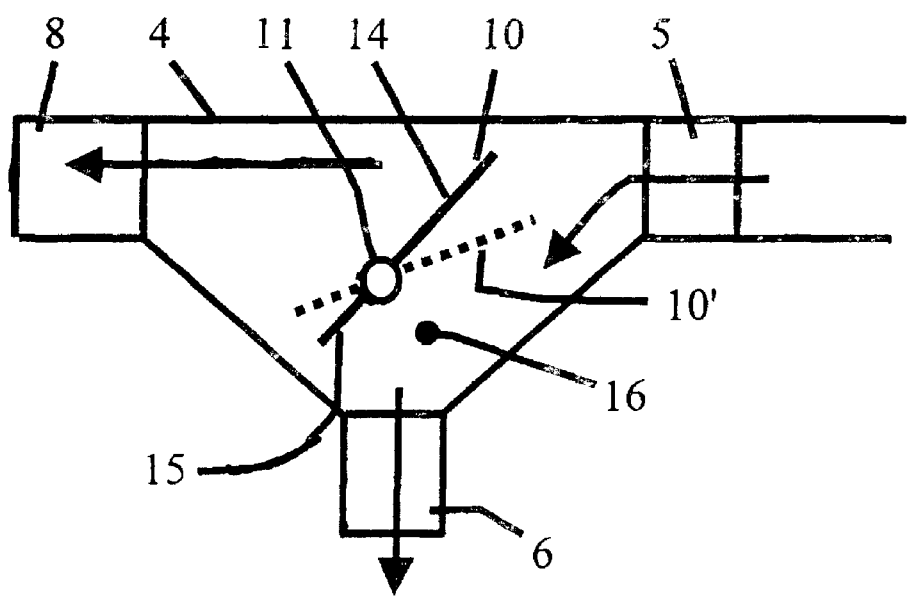
FIG. 2a shows details of the operating position of the vane of FIG. 1 during inspiration and FIG. 2b indicates the position during expiration.

The controller 4 and its operation will be described in more detail with reference to the FIGS. 2a and 2b in which the reference numerals of FIG. 1 are used to identify identical parts. The axle 11 is positioned part-way along the length of the vane 10 to divide the vane 10 into first and second sections 14, 15 as will be described below. The vane 10 and axle 11 are located in a widened mouth section 16, of the common inlet/outlet 6. As shown in FIG. 2a, during an inspiration phase of the breathing cycle gas from the inlet 5 is diverted to the common inlet/outlet 6 to be subsequently inspired. To achieve this the vane 10 is rotated so that its first section 14 is arranged to provide a flow path for the gas from the inlet 5 to the common inlet/outlet 6 (as illustrated by the solid construction of vane 10 in FIG. 2a). If the flow of gas supplied to the inlet 5 is greater than that required for inspiration then the vane 10 need not form a complete seal against the internal wall surface of the flow controller 4. The vane 10 is rotated sufficiently so that the first section 14 divides the gas flow between the common inlet/outlet 6 and the outlet 8 as shown, by the arrows representing the gas flow paths during an inspiration phase.

This excess gas flow is preferable since the first section 14 need not then be arranged to form a gas tight seal against flow of gas to the outlet 8 so reducing manufacturing tolerances; limiting the possibility of the vane 10 sticking; and speeding the response time of the vane 10 as friction is reduced.

During inspiration the second section 15 reduces the open area of the mouth 16 through which gas, deflected by the first section 14, can flow without passing out of the controller 4 through the common inlet/outlet 6.

At the end of the inspiration phase of a breathing cycle there is typically a pause before an expiration phase commences. In known ventilators, a positive pressure is often provided to the lungs that matches the end inspiration lung pressure. If it is desired to provide such a pressure in the ventilator of the present embodiment then the vane 10 may be rotated to a position in which the flow path is altered to provide the correct flow of gas to the common inlet/outlet 6, as shown by the broken line representation of the vane 10' in FIG. 2a.

Figure 2B:
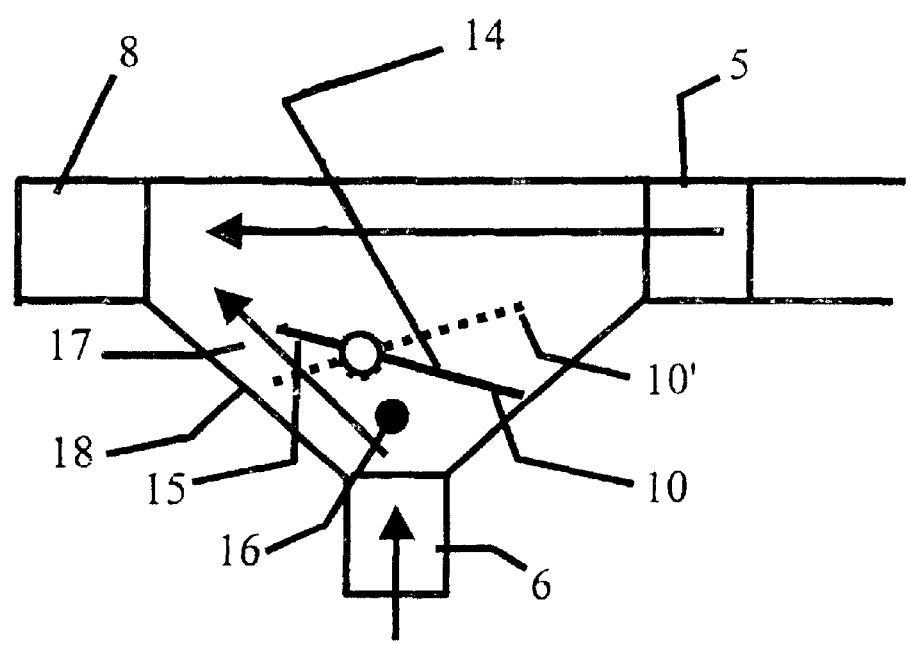

As illustrated in FIG. 2b, during an expiration phase the vane 10 is rotated so that most or all of the gas from the inlet 5 can flow along a path directly to the outlet 8 in a direction across a venturi outlet 17 for expiration gas flowing into the controller 4 through the common inlet/outlet 6. The gas flow paths during expiration is shown by the arrows in FIG. 2b. The first section 14 of the vane 10 effectively prevents gas flow from the inlet 5 to the common inlet/outlet 6 and the second section 15 co-operates with an internal wall section 18 of the controller 4 to define the venturi outlet 17 within the larger mouth 16 of the common inlet/outlet 6. The vane 10 is thus arranged so that in this position gas from the inlet 5 passes across the outlet 17 causing expiration gas to be drawn through the outlet 17 by venturi suction.

Thus, it will be appreciated by those skilled in the art that the gas from the inlet 5 provides a regulation (here an enhancement) of the expiration gas flow when directed across the expiration outlet 17. Rotation of the vane 10 so as to vary the size of the outlet 17 formed with the second section 15 of the vane 10 will vary the suction effect produced by any given flow from the outlet 5 so that the regulation of the flow of the expiration gas may be made variable in this embodiment of the present invention.

At the end of the expiration phase, it is common in the art of lung ventilation to provide a positive end expiratory pressure (PEEP) level in the lungs. This may be achieved in the present embodiment by rotating the vane 10 to a position as illustrated by the broken lines vane 10' in which the vane deflects a part of the flow from the inlet 5 into the common inlet/outlet 6 while allowing a greater portion of the gas to flow along a path between the inlet 5 and the outlet 6. Indeed the vane 10 may be rotated to this position at any time during the expiration phase to provide, as desired, a resistance to the passage of expiration gases from the outlet 17.

Figure 3:
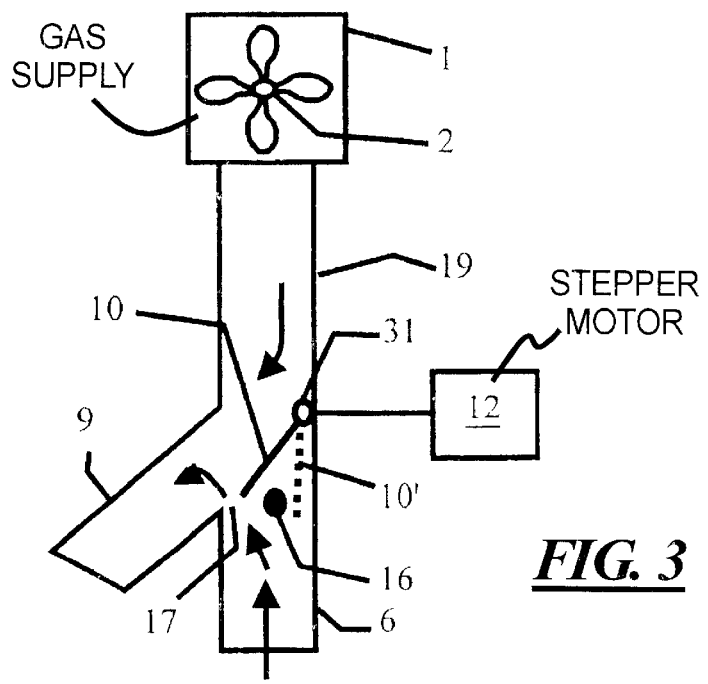
FIG. 3 shows a schematic representation of an alternative embodiment of the present invention.

An alternative embodiment of a ventilator according to the present invention is illustrated in FIG. 3 in which elements common to both FIG. 1 and FIG. 3 are given the same reference numerals. The ventilator has a gas supply 1 having a fan 2 for providing a continuous airflow throughout the breathing cycle of a patient. The fan 2 is at one end of a conduit 19 which connects to a mouth section 16 in fluid communication with a common inlet/outlet 6 and with an exhaust line 9. A vane 10 is located within the conduit 19 proximal the mouth 16 and is mounted at one end for rotation on an axle 31 of a stepper motor 12 to divide a flow of gas from the fan 2 between a path along the exhaust line 9 and a path through the common inlet/outlet 6 and to a breathing tube (not shown) and can provide variable amounts of gas flowing along each of these paths.

During an expiration phase the vane 10 is rotated to lie across the mouth 16 and form a venturi outlet 17 in cooperation with an internal wall of the conduit 19 as shown in FIG. 3. The vane 10 and the exhaust line 9 are relatively located so that when the outlet 17 is formed substantially all of the gas flow from the fan 2 can be deflected by the vane 10 across the outlet 17 and into the exhaust line 9 (as shown by the arrows in FIG. 3). As with the embodiment of FIG. 1, the flow of gas from the fan 2 in a direction across the outlet 17 draws in expiration gas from the breathing tube (not shown) and thereby reduces the expiration effort of the patient.

During an inspiration phase, the vane 10 is rotatable to unblock the common inlet/outlet 6 (as shown by the broken line representation of the vane 10' in FIG. 3) so that the flow from the fan 2 is allowed to pass through the common inlet/outlet 6 and into the breathing tube 7. By varying the degree of rotation of the vane 10 the flow of gas from the fan 2 can be divided between the two above described paths in different amounts, for example to achieve a PEEP level or to provide an end inspiration lung pressure.

Figure 4:
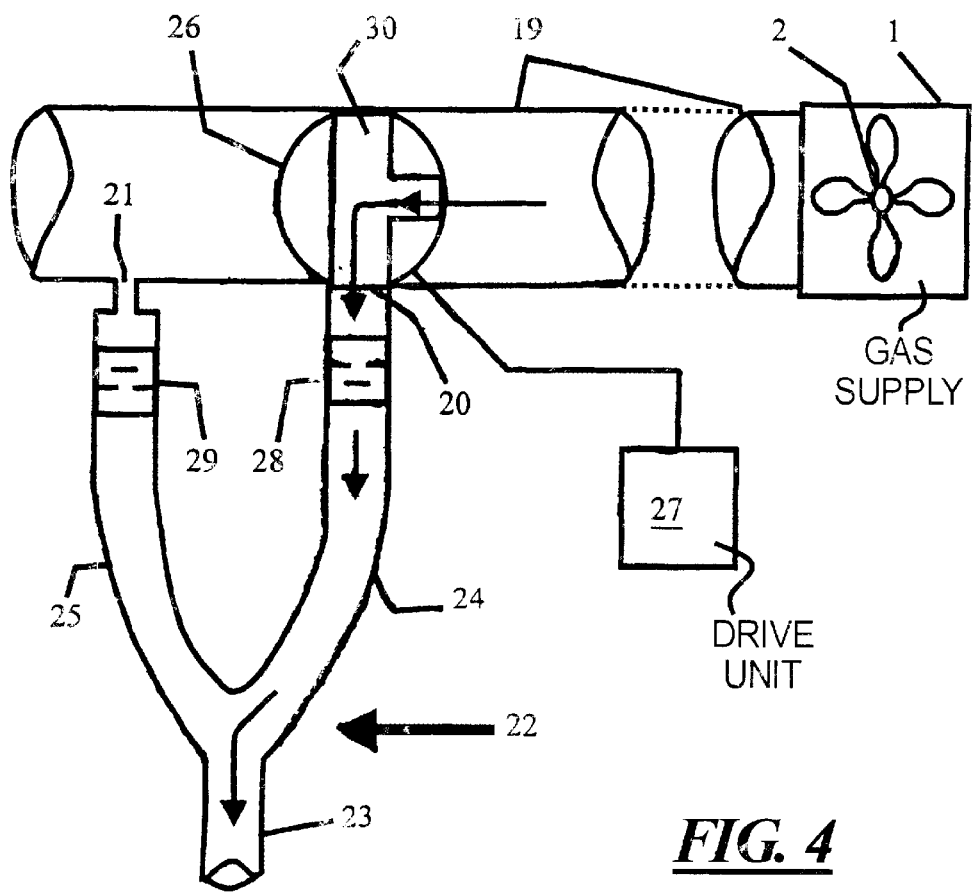
FIG. 4 shows a schematic representation of a further alternative embodiment of the present invention.

FIG. 4 illustrates an alternative to the vane-type flow controller of FIG. 1 and FIG. 3 which also shows a further embodiment of a ventilator according to the present invention. A flow conduit 19 is connected at one end to the output of a gas supply means 1 comprising a fan 2 which is operated to provide a flow in the conduit 19 throughout the breathing cycle. Along the length of the conduit 19 are separate, spaced apart openings which respectively constitute an inlet 20 for supplying inspiration gas from the conduit 19 to a breathing tube 22 and a venturi outlet 21 through which expiration gas from the tube 22 may pass into the conduit 19. The tube 22 is formed with a common flow conduit 23 and arms 24, 25 connecting the common flow conduit to the inlet 20 and the outlet 21, respectively.

A known T-valve flow controller 26 is placed in the flow conduit 19 in operable connection with the outlet 20. The valve is operable by means of a motor drive unit 27 to move between a position in which a flow path is created for gas from the supply 1 which leads some or all of that gas into the breathing tube 22 (illustrated by the arrows in FIG. 4) and a position in which a flow path is created which leads gas from the supply 1 across the outlet 21. Preferably, one way valves 28, 29 are placed in the arms 24, 25 respectively to ensure gas flow in each of the arms 24, 25 in one direction only.

The ventilator operates as follows: during an inspiration phase, the T-valve 30 of the controller 26 is rotated so that gas from the supply means 1 can flow through the valve 30 and into the inlet 20 to provide gas for inspiration. During expiration the T-valve 30 of the controller 26 is rotated so that gas from the supply 1 can flow through the conduit 19 and across the outlet 21. Expiration gas may then be drawn through the outlet 21 into the conduit 19 by venturi suction.

The above embodiments have all been described in relation to a gas supply that has a continuously rotating fan. It will, however, be appreciated by those skilled art that the invention is not restricted to this embodiment and that a ventilator may be provided using any suitable gas source that can operate to supply a gas flow for at least that part of the expiration phase during which it is desired to achieve regulation of the flow of expiration gas while still remaining within the scope of the invention.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for supplying breathing gas to a subject comprising:

a gas supply for generating a flow of breathable gas during an inspiration phase;

an inspiration line having an inlet through which said flow of breathing gas from said gas supply can pass;

an expiration line adapted to receive expiration gas from a subject;

a flow controller for selecting, during an inspiration phase, a first flow path for said breathable gas from said gas supply into said inlet;

said gas supply also providing a flow of gas during an expiration phase;

said expiration line containing a venturi outlet disposed in gaseous communication with said flow controller; and said flow controller, during an expiration phase, selecting a second flow path for said flow of gas from said gas supply in a direction across said venturi outlet to enhance removal of expiration gas by venturi suction.

2. An apparatus as claimed in claim 1 wherein said gas supply continuously generates said flow of breathable gas during said inspiration phase and as said flow of gas in said expiration phase.

3. An apparatus as claimed in claim 2 wherein said gas supply comprises a fan assembly.

4. An apparatus as claimed in claim 2 wherein said gas supply provides said flow of breathable gas during said inspiration phase in an amount greater than an amount needed for supply to a subject.

5. An apparatus as claimed in claim 2 wherein said controller comprises a movable vane deflector which is movable within a path of said flow of breathable gas from said gas supply to selectively couple said flow of breathable gas to said first flow path and to said second flow path.

6. An apparatus as claimed in claim 5 wherein said inlet and said venturi outlet communicate with a common opening, and wherein said vane is pivotably mounted for rotation around an axis between a first position in which said flow of breathable gas is coupled to the first flow path and a second position in which said vane cooperates with said common opening to form said venturi outlet, and in which said flow of breathable gas is coupled to said second flow path.

7. An apparatus as claimed in claim 6 wherein said vane is pivotably mounted on a shaft disposed between a first end and a second end of said vane, and is rotatable to move said first end to direct said flow of breathable gas into said common opening during said inspiration phase, and wherein said second end forms said venturi outlet and directs said flow across said outlet.

* * * * *